US009305347B2

(12) United States Patent
Parma et al.

(10) Patent No.: US 9,305,347 B2
(45) Date of Patent: Apr. 5, 2016

(54) AUTOMATIC VOLUMETRIC IMAGE INSPECTION

(71) Applicant: Dental Imaging Technologies Corporation, Hatfield, PA (US)

(72) Inventors: Michael Parma, Chalfont, PA (US); Robert Keating, Chalfont, PA (US); Edward S. Walsh, Media, PA (US); Richard H. Elvin, Quakertown, PA (US); Michael S. O'Donnell, Macungle, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 308 days.

(21) Appl. No.: 13/766,628

(22) Filed: Feb. 13, 2013

(65) Prior Publication Data
US 2014/0225892 A1 Aug. 14, 2014

(51) Int. Cl.
*G06T 7/00* (2006.01)
*A61B 6/03* (2006.01)
(Continued)

(52) U.S. Cl.
CPC ............... *G06T 7/0012* (2013.01); *A61B 6/032* (2013.01); *A61B 6/14* (2013.01); *A61B 6/463* (2013.01); *A61B 6/5223* (2013.01); *G06T 19/00* (2013.01); *G06T 2210/41* (2013.01)

(58) Field of Classification Search
CPC .................. G06T 7/0012; G06T 2207/10072; G06T 2207/10081; A61B 6/12; A61B 19/50
See application file for complete search history.

(56) References Cited

U.S. PATENT DOCUMENTS 6,424,692 B1 7/2002 Suzuki
6,891,963 B1 5/2005 Goto et al.
(Continued)

FOREIGN PATENT DOCUMENTS

CN 1657012 A 8/2005
CN 102525662 A 7/2012
(Continued)

OTHER PUBLICATIONS

Extended European Search Report for European Application No. 14154364.5 dated Jun. 27, 2014 (6 pages).
(Continued)

*Primary Examiner* — Maurice L McDowell, Jr.
*Assistant Examiner* — Raffi Isanians
(74) *Attorney, Agent, or Firm* — Michael Best & Friedrich LLP

(57) ABSTRACT

Systems and methods for inspecting data generated during a scan of an object. One system includes a processor. The processor is configured to receive projection data generated by a CT scan of an object, generate a three-dimensional, volumetric data set based on the projection data, and automatically generate a plurality of cinematic frames of a cinematic sequence based on the three-dimensional, volumetric data set. Each of the plurality of cinematic frames has a different value for at least one parameter. The processor is also configured to automatically generate a signal to display the cinematic sequence in a frame-by-frame manner. In some embodiments, the processor continuously displays the cinematic sequence until a user accepts the three-dimensional, volumetric data set or stops the cinematic sequence (e.g., to perform a manual inspection of the three-dimensional, volumetric data set and/or re-initiate a scan of the object).

30 Claims, 15 Drawing Sheets

(51) Int. Cl.
*A61B 6/14* (2006.01)
*A61B 6/00* (2006.01)
*G06T 19/00* (2011.01)

(56) References Cited

U.S. PATENT DOCUMENTS

| | | | |
|---|---|---|---|
| 7,336,763 B2 | 2/2008 | Spartiotis et al. | |
| 7,668,285 B2 * | 2/2010 | Mukumoto | 378/4 |
| 8,160,320 B2 | 4/2012 | Li | |
| 2007/0040854 A1 | 2/2007 | Lievin et al. | |
| 2007/0109294 A1 | 5/2007 | Gotman et al. | |
| 2008/0117225 A1 | 5/2008 | Wegenkittl et al. | |
| 2008/0130833 A1 * | 6/2008 | Wang | 378/98.2 |
| 2010/0302245 A1 * | 12/2010 | Best | 345/426 |
| 2012/0159391 A1 * | 6/2012 | Berry et al. | 715/823 |

FOREIGN PATENT DOCUMENTS

| | | |
|---|---|---|
| JP | 2004215961 | 8/2004 |
| JP | 2004215961 A | 8/2004 |
| JP | 2007029487 | 2/2007 |
| JP | 2007029487 A | 2/2007 |
| JP | 4342016 | 7/2009 |
| JP | 4497570 | 4/2010 |
| KR | 10-2009-0077025 | 7/2009 |
| WO | 2009044316 | 4/2009 |

OTHER PUBLICATIONS

Office Action from Korean Patent Office for Application No. 10-2014-14615 dated Dec. 10, 2014 (8 pages).

Office Action from Japanese Patent Office for Application No. 2014-018404 dated Jan. 8, 2015 (8 pages).

Final Office Action with English translation from the Japanese Patent Office for Application No. 2014-018404 dated Sep. 17, 2015 (4 pages).

1st Office Action from the State Intellectual Property Office of the People's Republic of China for Application No. 201410050282.6 dated Sep. 1, 2015 (16 pages).

* cited by examiner

FIG. 5

AUTOMATIC VOLUMETRIC IMAGE INSPECTION

FIELD

Embodiments of the invention relate to medical imaging systems, such as dental imaging systems. In particular, embodiments of the invention relate to systems and methods for automatically inspecting volumetric dental images.

BACKGROUND

A conventional computed tomography ("CT") system captures three-dimensional data of a patient. After acquiring the information, an operator reviews the data to ensure that the CT scan includes the necessary data for treating a particular patient. To review or inspect the acquired data, existing systems generate a set of two-dimensional renderings of a volumetric image generated from the scan. The operator, however, must adjust the views of the image to visually inspect the volumetric image for quality and proper positioning of the patient for the intended purpose of the scan. Manually selecting particular views or aspects of the volumetric image takes time, which prolongs the patient's CT scan (i.e., the patient is typically not allowed to leave the CT scanning apparatus until the operator assures that the captured data is appropriate). Prolonging the time of the scan prolongs the patient's discomfort and reduces the throughput of the CT scanning apparatus. In addition, the manual inspection delays the transfer of the volumetric image to an external storage location, which delays the availability of the image on other workstations.

SUMMARY

Embodiments of the present invention provide methods and systems for automatically inspecting three-dimensional data generated based on a computed tomography ("CT") scan of an object, e.g., a patient's head. One embodiment provides a system for inspecting data generated during a scan of an object. The system includes a processor. The processor is configured to receive projection data (i.e., a set of x-ray projection frames, plus the positions of the x-ray source and the x-ray detector for each projection frame) generated by a CT scan of an object, generate a three-dimensional, volumetric data set from the projection data, and automatically generate a plurality of cinematic frames based on the three-dimensional, volumetric data set to form a cinematic sequence. Each of the plurality of cinematic frames has a different value for at least one parameter (e.g., angle of rotation of the object, position within the object, brightness level, magnification level, etc.). The processor is also configured to automatically generate a signal to display the cinematic sequence in a frame-by-frame manner (e.g., on a touchscreen or other display). In some embodiments, the processor continuously displays the cinematic sequence until a user accepts the three-dimensional, volumetric data set or stops the sequence (e.g., to perform a manual inspection of the three-dimensional, volumetric data set and/or re-initiate a scan of the object).

Another embodiment provides a method for inspecting data generated during a scan of an object. The method includes receiving, by a processor, projection data generated by a CT scan of an object; generating, by the processor, a three-dimensional, volumetric data set from the projection data; and automatically, by the processor, generating a plurality of cinematic frames to form a cinematic sequence based on the three-dimensional, volumetric data set, wherein each of the plurality of cinematic frames has a different value for at least one parameter. The method further includes automatically generating a signal to display the cinematic sequence in a frame-by-frame manner.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 illustrates a select-patient screen.

DETAILED DESCRIPTION

Figure 1:
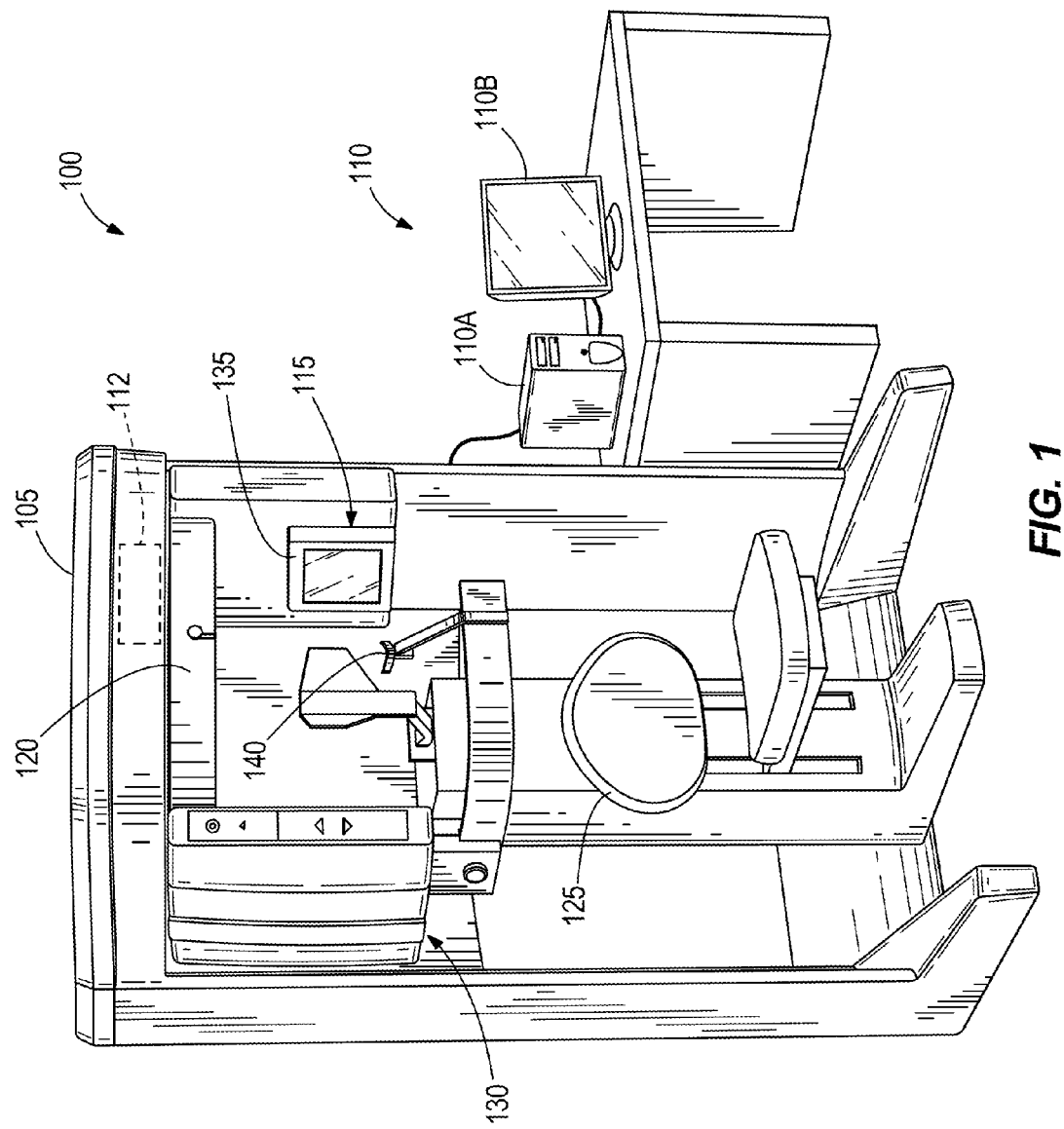
FIG. 1 illustrates a medical imaging system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

FIG. 1 illustrates a medical imaging system 100. The system 100 includes an imaging apparatus 105 and a workstation 110. The imaging apparatus 105 includes a computed tomography ("CT") scanner that scans an object. The workstation 110 includes a computer 110A and a display, e.g., a touchscreen 110B. In some embodiments, the computer 110A and the touchscreen 110B are combined in a single device. Also, in some embodiments, the workstation 110 includes peripheral devices, e.g., a keyboard, mouse, printer, etc., connected to the computer 110A and/or the touchscreen 110B. In addition, it should be understood that in some embodiments, a non-touch-sensitive screen or monitor is used in place of or in addition to the touchscreen 110B. As described in more detail below with respect to FIG. 2, the computer 110A is configured to receive projection data generated by the imaging apparatus 105, generate three-dimensional, volumetric data from the projection data, construct an image based on the three-dimensional, volumetric data, and display the image on the touchscreen 110B. In some embodiments, the computer 110A is also configured to control operation of the imaging apparatus 105 (e.g., based on user input). The computer 110A can be connected to the imaging apparatus 105 by one or more wired or wireless connections.

The imaging apparatus 105 is, for example, a dental CT device and includes an on-board computer or processor 112, a radiation detector 115, a gantry 120, a support 125 for an object or patient being imaged, and a radiation source 130. The radiation detector 115 is positioned on the gantry 120 opposite the radiation source 130 includes a detector array 135 having a plurality of detection elements. During a scan, a patient either sits on the support 125 or stands (and places his or her chin in a chin support 140). However, the invention is not limited to systems designed to accommodate seated or standing patients. For example, in some embodiments, the patient can lie down. The gantry 120 is rotated around the patient's head, and, as the gantry 120 rotates, the radiation source 130 moves and directs radiation at the patient's head at various angles. The radiation detector 115 detects the radiation passing through the patient and generates a set of projection frames, which are sent to the on-board computer or processor 112 within the imaging apparatus 105. The on-board computer 112 receives the raw projection frames and also keeps track of the positions of the radiation source 130 and the detector 115. During or after the scan, the on-board computer 112 sends projection data, which comprises the projection frames and the positions of the radiation source 130 and the detector 115, to the workstation computer 110A.

Figure 2:
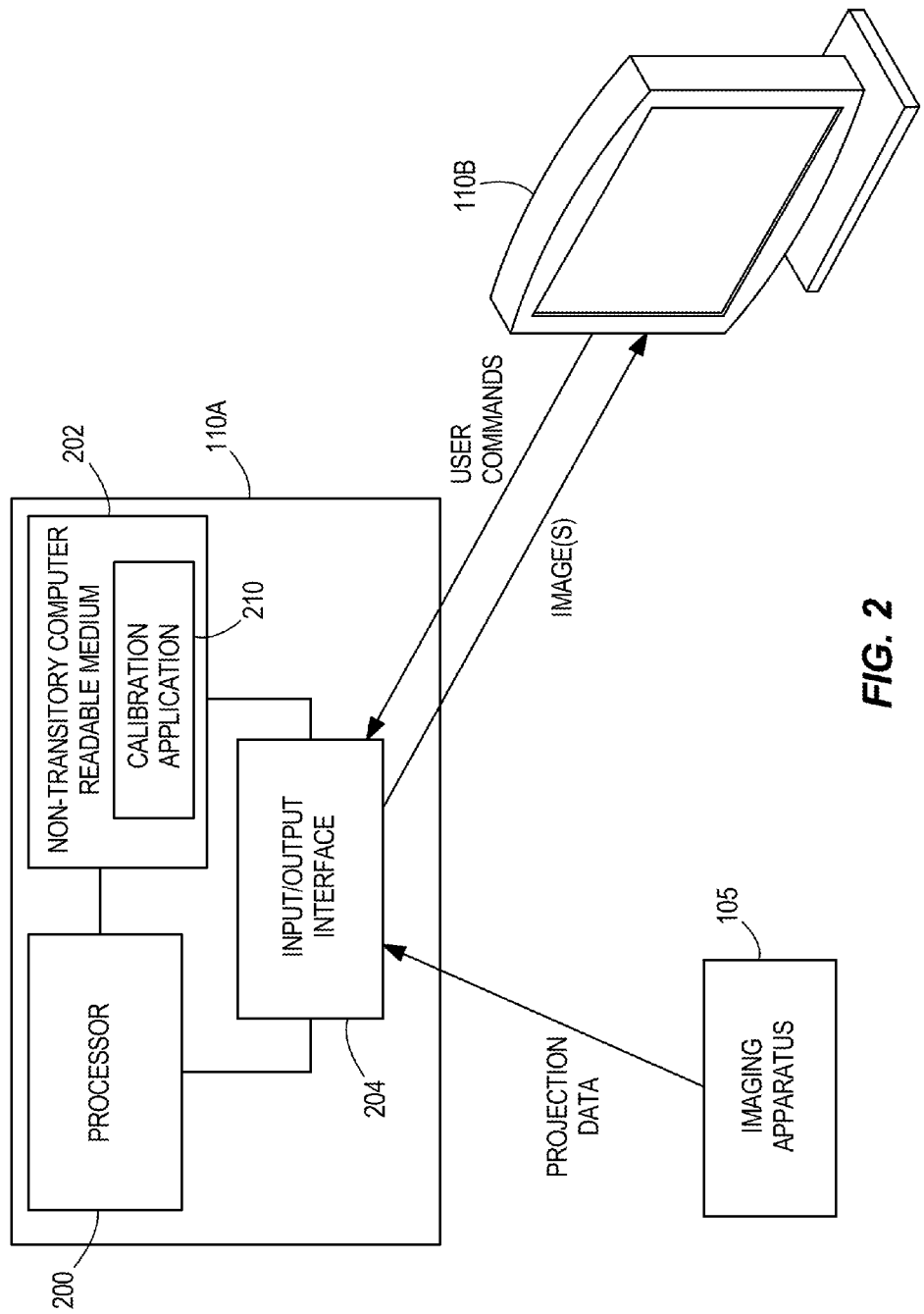
FIG. 2 schematically illustrates the medical imaging system of FIG. 1.

As illustrated in FIG. 2, the computer 110A includes a processor 200, non-transitory computer-readable medium 202, and an input/output interface 204. It should be understood that in other constructions, the computer 110A includes additional, fewer, or different components. The processor 200 is configured to retrieve instructions and data from the media 202 and execute, among other things, the instructions to receive projection data from the imaging apparatus 105, generate three-dimensional volumetric data from the projection data, and output data to the touchscreen 110B. The input/output interface 204 transmits data from the processor 200 to external systems, networks, and/or devices and receives data from external systems, networks, and/or devices. In particular, the input/output interface 204 communicates with the imaging apparatus 105 and the touchscreen 110B over one or more wired or wireless connections and/or networks. The input/output interface 204 can also store data received from external sources to the media 202 and/or provide the data to the processor 200. The computer-readable media 202 stores program instructions and data including a user interface ("UI") application (or "application") 210. When executed by the processor 200, the UI application 210 receives user commands and displays images and other information to a user on the touchscreen 110B.

Figure 3:
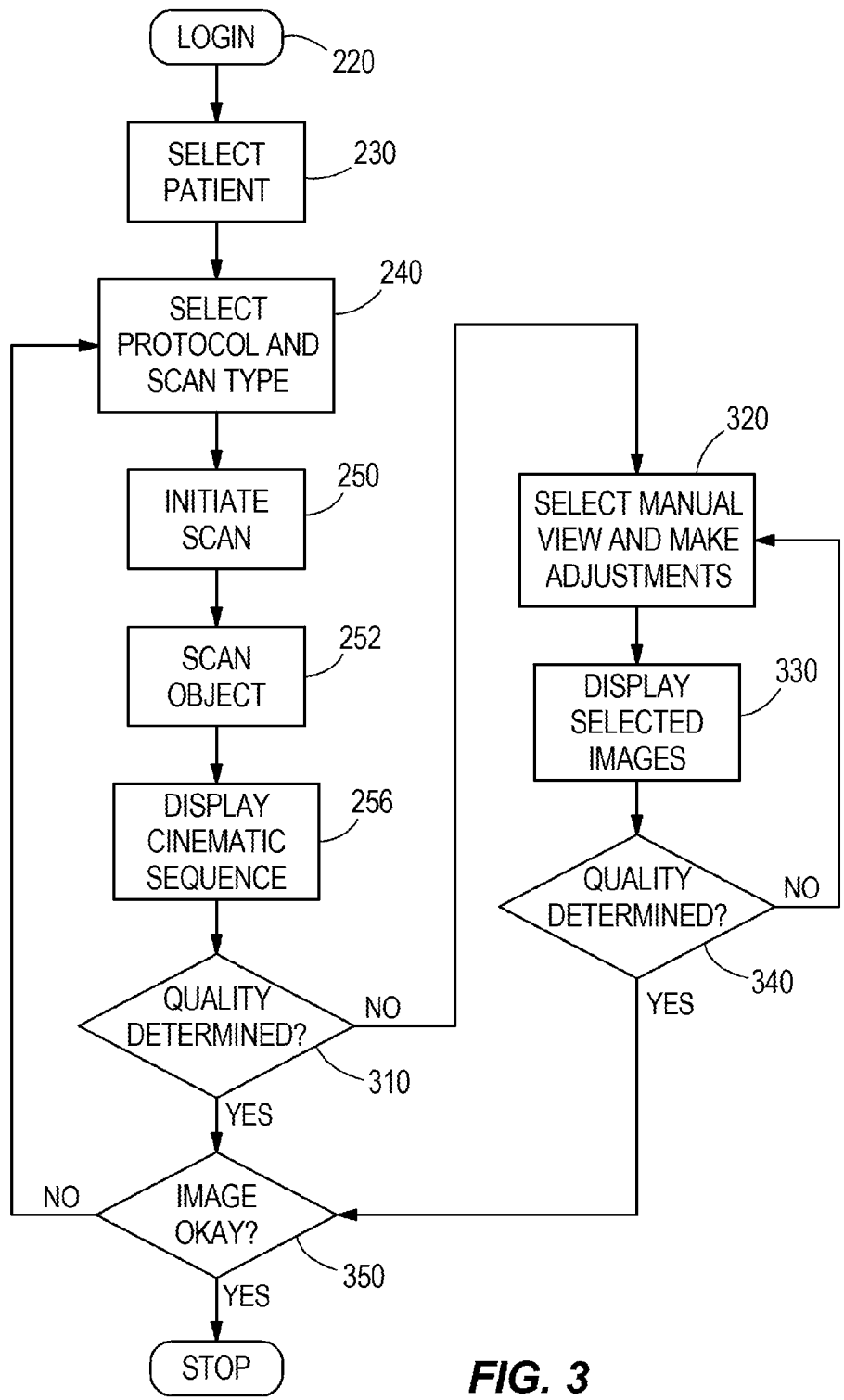
FIG. 3 is a flow chart illustrating a method of inspecting a data set generated during a scan performed by the medical imaging system of FIG. 1.
Figure 4:
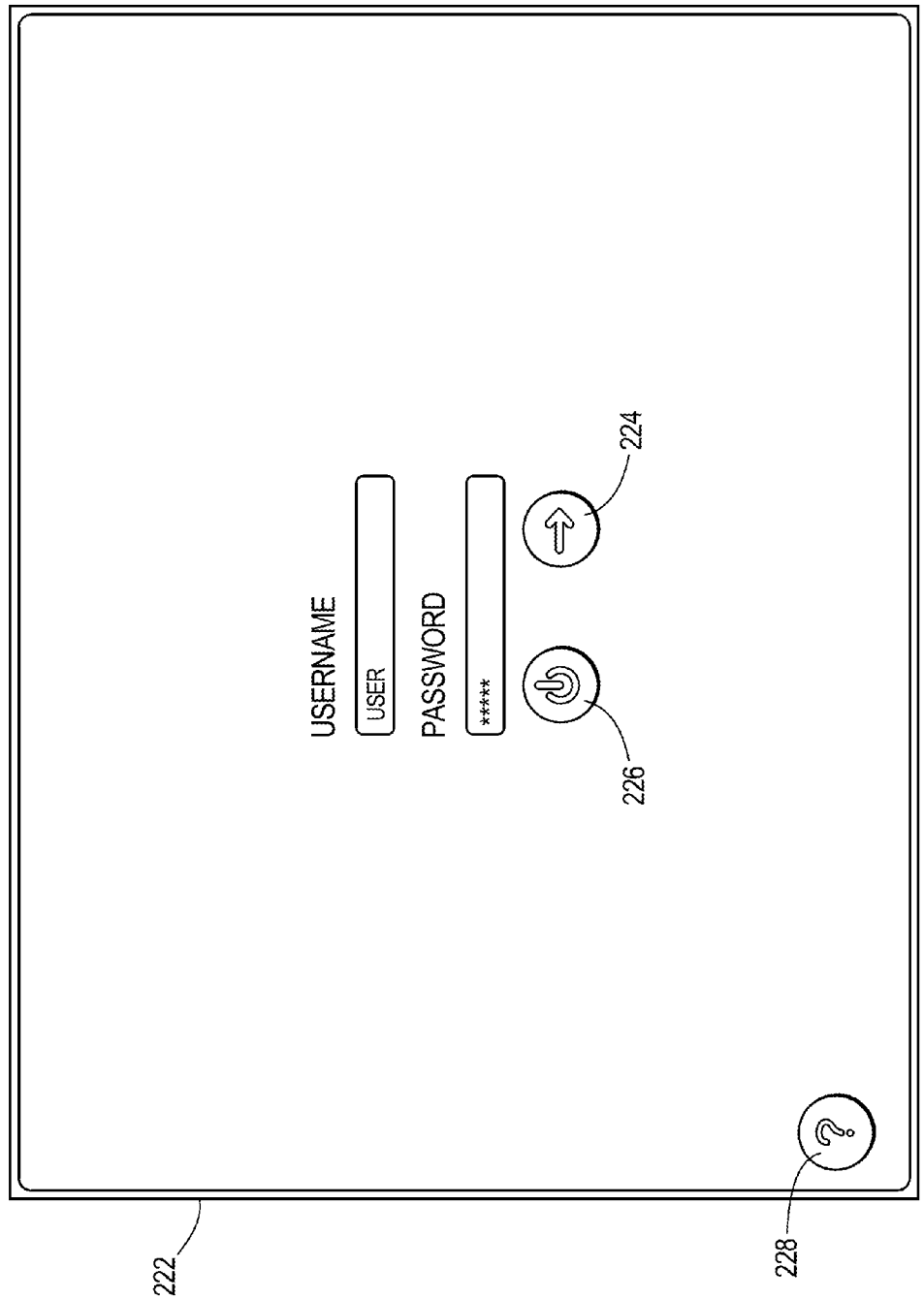
FIG. 4 illustrates a login screen.

The system 100 can be used initiate a CT scan and inspect the data set generated from the scan. In particular, the processor 200 included in the computer 110A executes the user interface application 210 to display various screens to a user on the touchscreen 110B. A user enters commands through the displayed screens using buttons on the screens (selectable through the touchscreen 110B itself or separate peripheral devices, e.g., a keyboard or a mouse) to initiate a scan and inspect the data acquired during the scan. As illustrated in FIG. 3, to start the process, a user logs into the user application 210 (at step 220). For example, FIG. 4 illustrates a login screen 222 generated and displayed by the application 210. The login screen 222 prompts the user for a username and password and includes a next or enter button 224. In some embodiments, the login screen 222 also includes a power-off button 226 and a help button 228.

It is to be noted that, although the foregoing description refers to a user controlling the medical imaging system 100 through the computer 110A, the system 100 can also include its own on-board user interface to allow a user to control the system 100 directly. Control through the on-board user interface can be instead of, or in addition to, control through the computer 110A.

Figure 5:
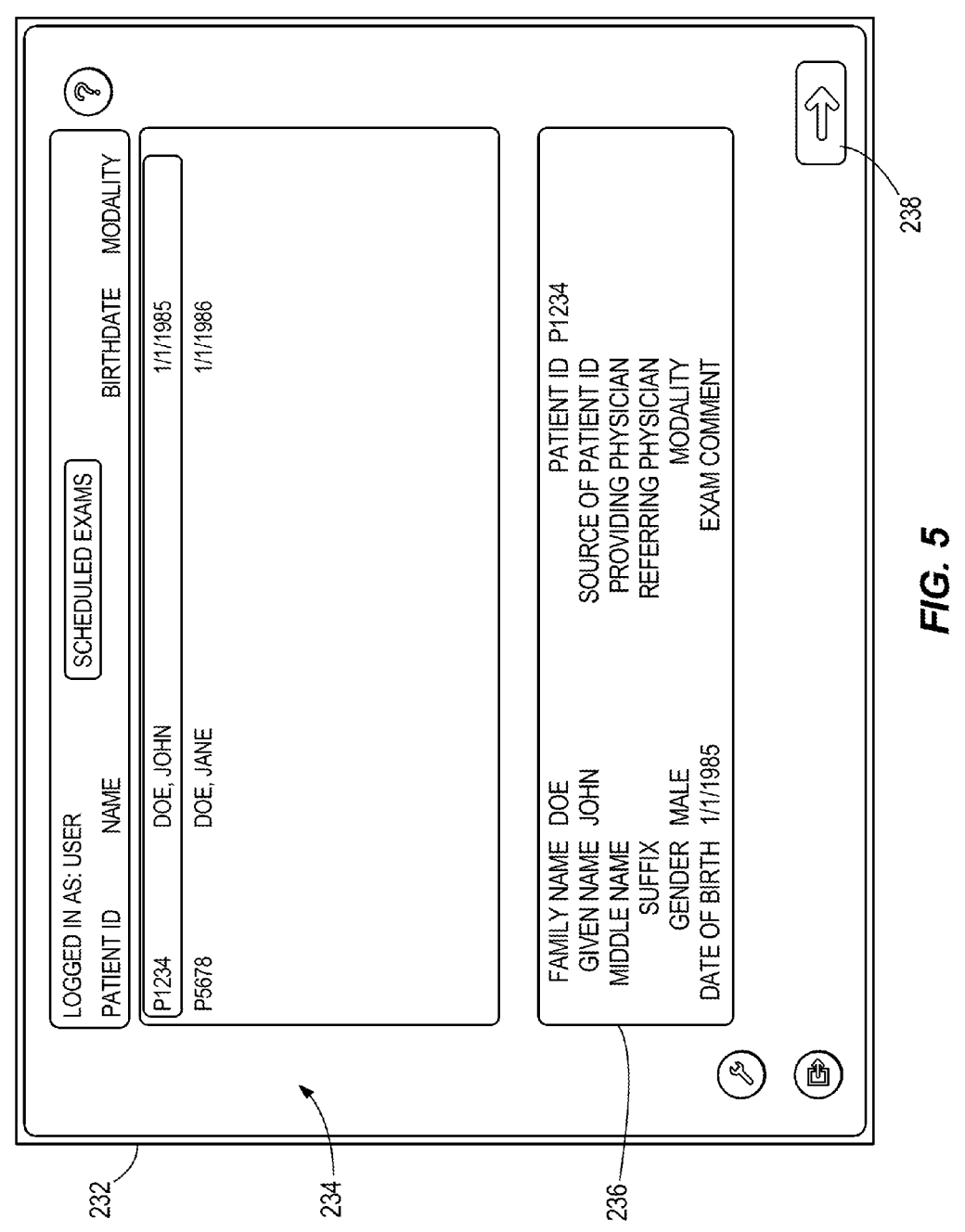

After the user logs in, the user selects a patient (at step 230). For example, FIG. 5 illustrates a select-patient screen 232 generated and displayed by the application 210. The screen 232 includes a list 234 of scheduled scans or exams. In some embodiments, the scheduled scans or exams are provided by a separate system or device, e.g., a picture archiving and communication system ("PACS") or a patient management system. As illustrated in FIG. 5, the screen 232 also includes a detail section 236 that provides additional data regarding a particular patient included in the list 234. After selecting a patient from the list 234 (e.g., by clicking on a listed patient), the user can select a next button 238.

Figure 6:
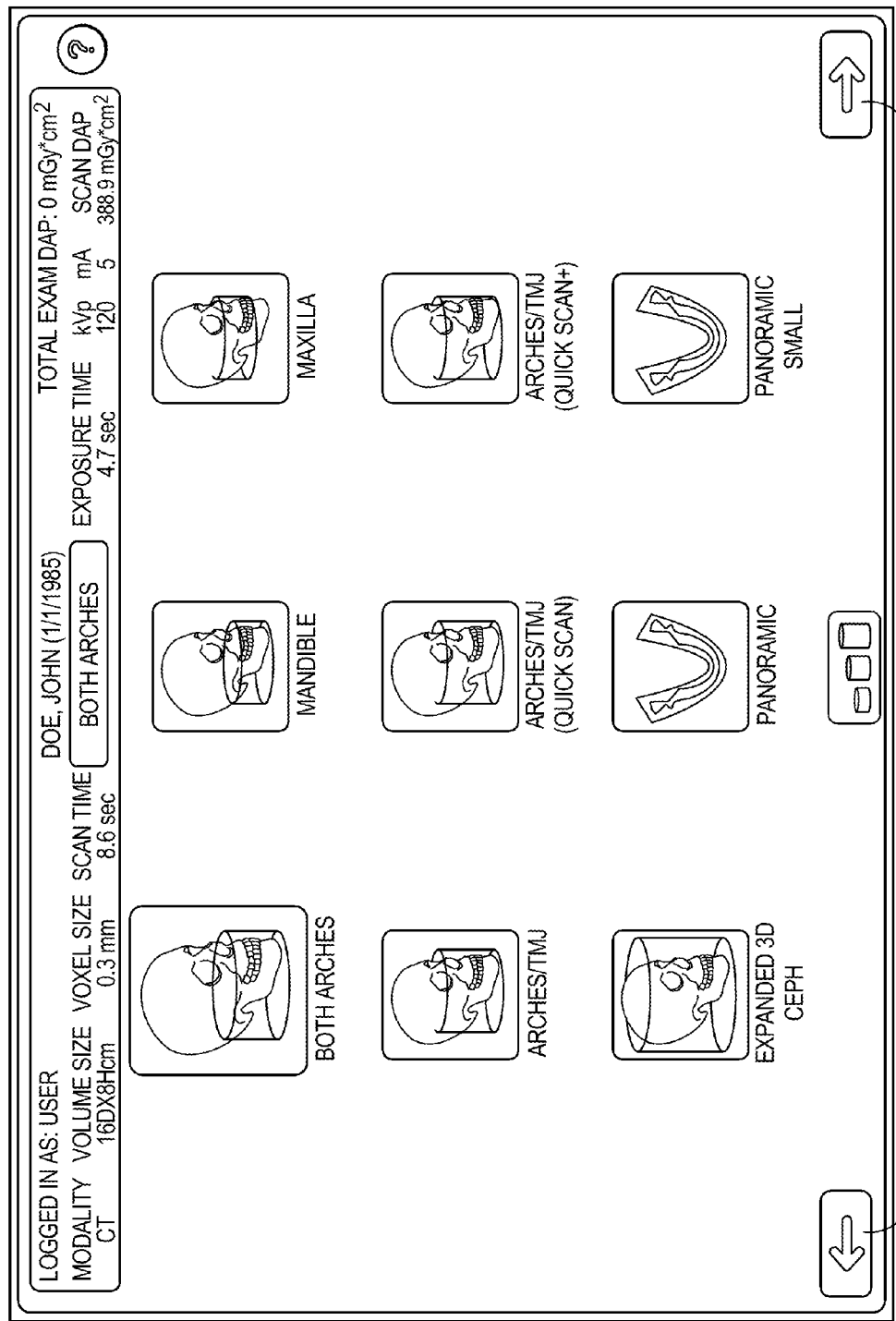
FIG. 6 illustrates a select-protocol screen.
Figure 7:
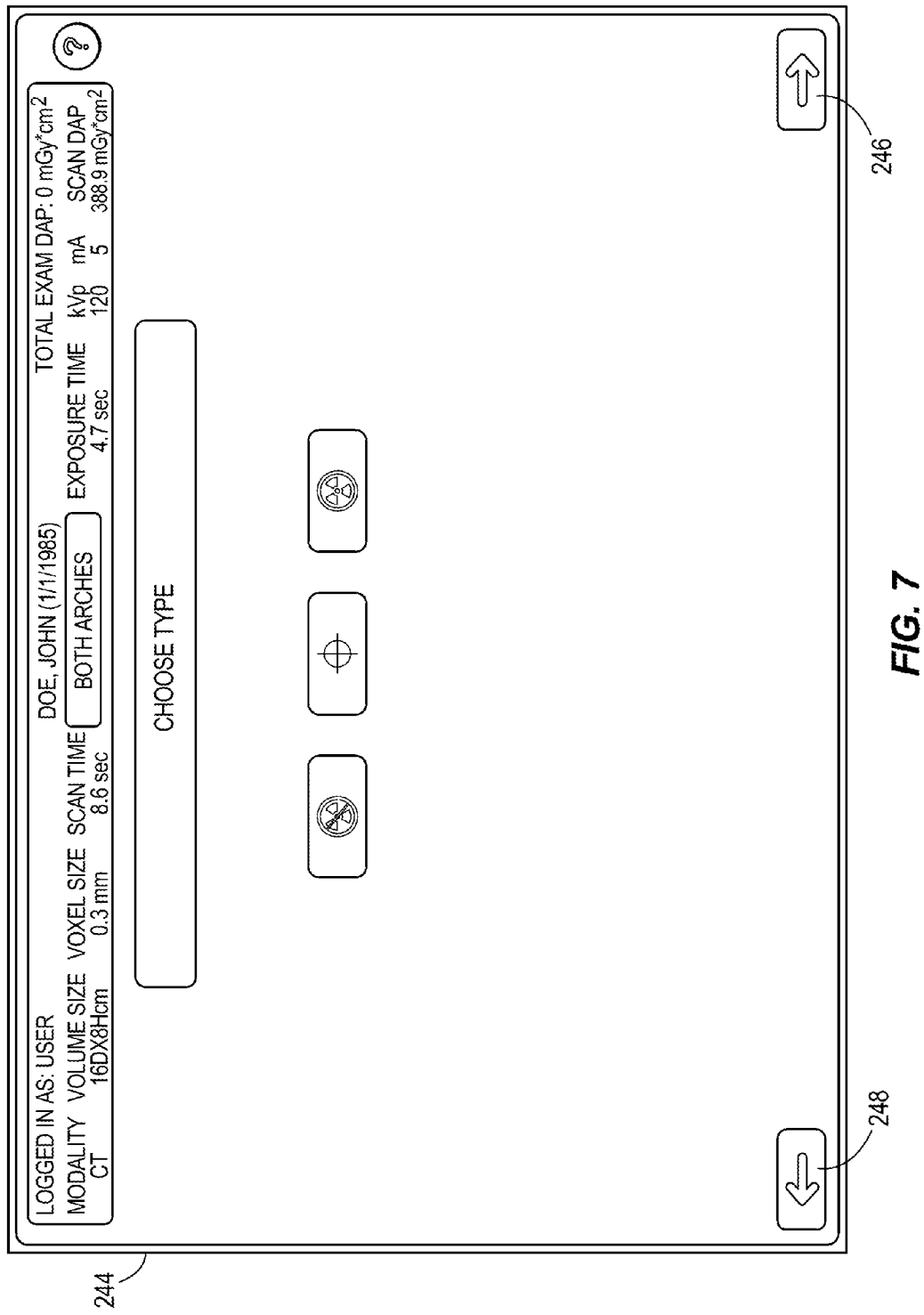
FIG. 7 illustrates a select-scan-type screen.

The user also selects a scan protocol and a scan type (at step 240). For example, FIG. 6 illustrates a select-protocol screen 242 generated and displayed by the application 210, and FIG. 7 illustrates a select-scan-type screen 244 generated and displayed by the application 210. Both screens 242 and 244 include a next button 246 that the user can select after making a selection on a particular screen. In addition, the screen 242 and 244 each include a back button 248 that the user can select to return to a previously-displayed screen. In some embodiments, one or more of the scan protocols are pre-selected by a user and set as "favorites" for the user. Therefore, when the user logs into the application 210, the application 210 includes the user's predefined "favorites" on the select-protocol screen 242.

Figure 8:
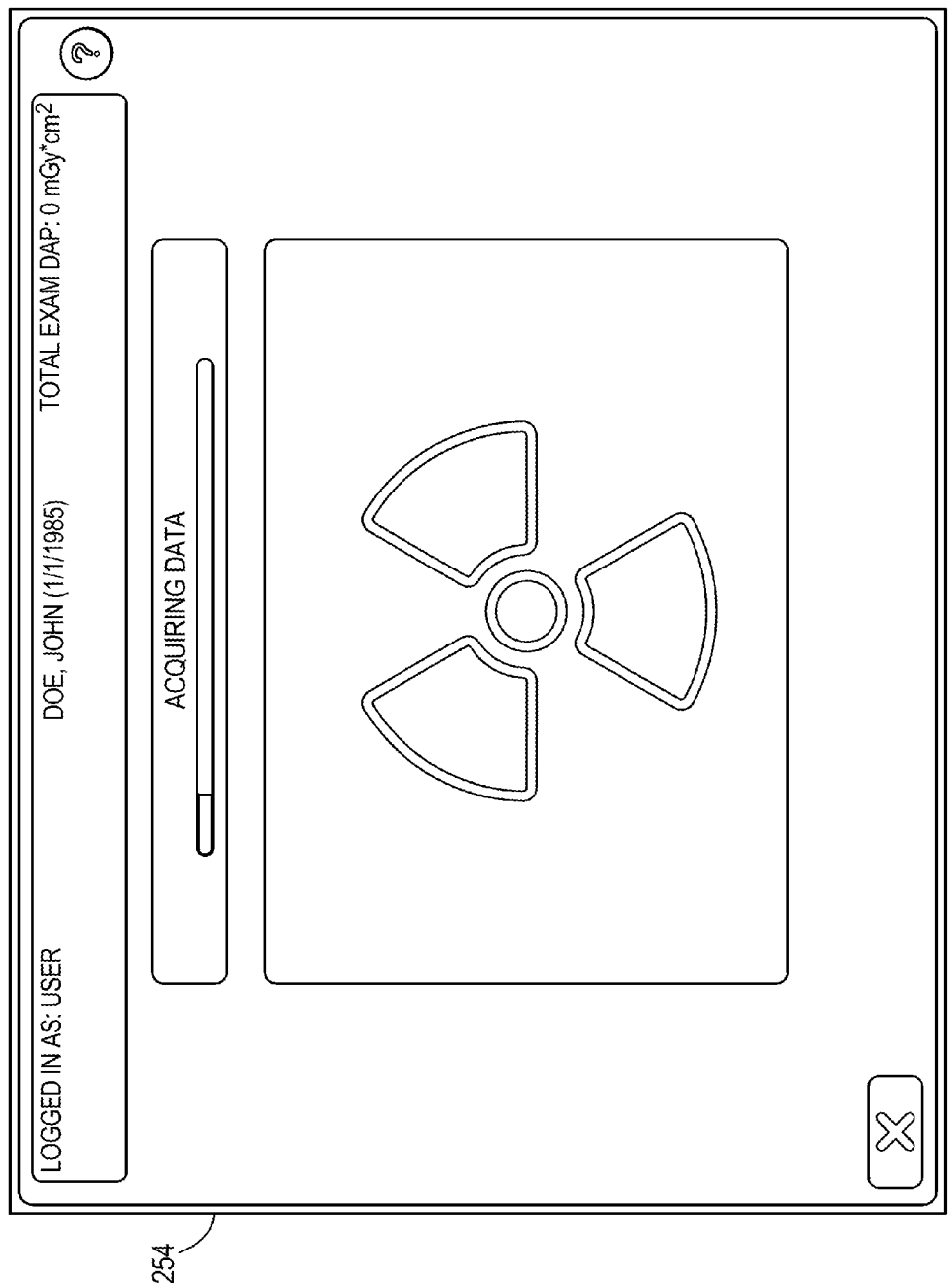
FIG. 8 illustrates an acquiring-data screen.

After the user selects the patient, scan protocol, and scan type, the user initiates the scan (e.g., by selecting the next button 246 on the select-scan-type screen 244) (at step 250). To start the scan, the application 210 communicates with the imaging apparatus 105 to initiate a scan as specified by the user (at step 252). In some embodiments, the application 210 displays an acquiring-image screen 254, as illustrated in FIG. 8, while the scan is performed and while the application 210 receives the projection data from the imaging apparatus 105.

As described above, application 210 generates a three-dimensional, volumetric data set based on the projection data, automatically generates a plurality of cinematic frames to form a cinematic sequence based on the three-dimensional, volumetric data set, and automatically generates a signal to display the cinematic sequence to the user (at step 256). The user uses the cinematic sequence to inspect the quality and position of the three-dimensional, volumetric data set to ensure that the CT scan was performed properly. In particular, the cinematic sequence can include aspects of a three-dimensional, volumetric data set useful for assessing the quality and positioning of the scan. For example, the cinematic sequence can include cinematic frames representing predefined angles of rotation of the patient's head (e.g., left side, front, and right side) or predefined slices of the patient's head that provide a useful sampling of the three-dimensional, volumetric data set. However, because the user is not required to manually select aspects of the three-dimensional, volumetric data set (e.g., aspects of a volumetric image defined by the data set) for inspection, the application 210 increases the speed and efficiency of inspecting the results of a CT scan and the overall scanning procedure.

Figure 9:
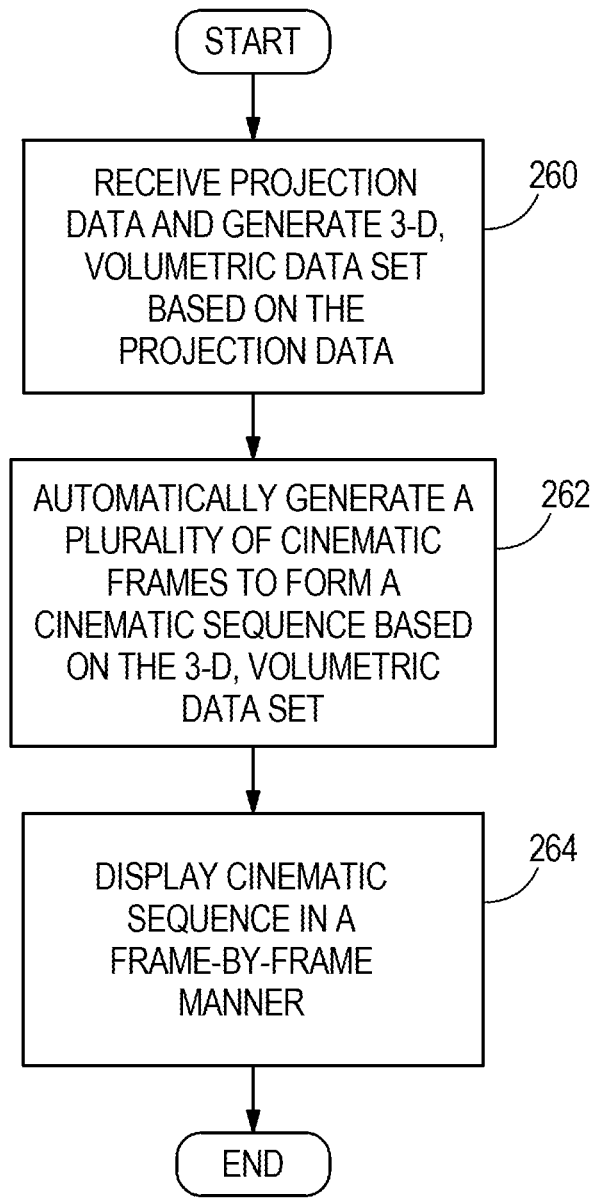
FIG. 9 illustrates a method of generating a cinematic sequence.

In particular, as illustrated in FIG. 9, the application 210 receives projection data generated by a CT scan of an object and generates a three-dimensional, volumetric data set from the projection data (at step 260). Based on the three-dimensional, volumetric data set, the application 210 automatically generates a plurality of cinematic frames to form a cinematic sequence (at step 262). In some embodiments, the cinematic frames are two-dimensional renderings of the three-dimensional, volumetric data set. In other embodiments, the cinematic frames are slices of the three-dimensional, volumetric data set. Each of the plurality of cinematic frames has a different value for at least one parameter to provide the user with a sampling of the three-dimensional, volumetric data set. For example, in some embodiments, each of the plurality of cinematic frames has a different value for an angle of rotation of the patient's head. In other embodiments, each of the plurality of cinematic frames has a different value for a position within the patient's head. Furthermore, the cinematic frames can have different magnification levels, fields-of-view, colors, color scales, brightness levels, contrast levels, translational vantage points, etc. Accordingly, each frame of the cinematic sequence provides a particular aspect of the three-dimensional, volumetric data set that can be inspected by the user. In some embodiments, the user selects the differentiating parameter of the cinematic frames before initiating the scan. In other embodiments, the differentiating parameter of the cinematic frames is defined based on the selected scan protocol and/or scan type.

Figure 10A:
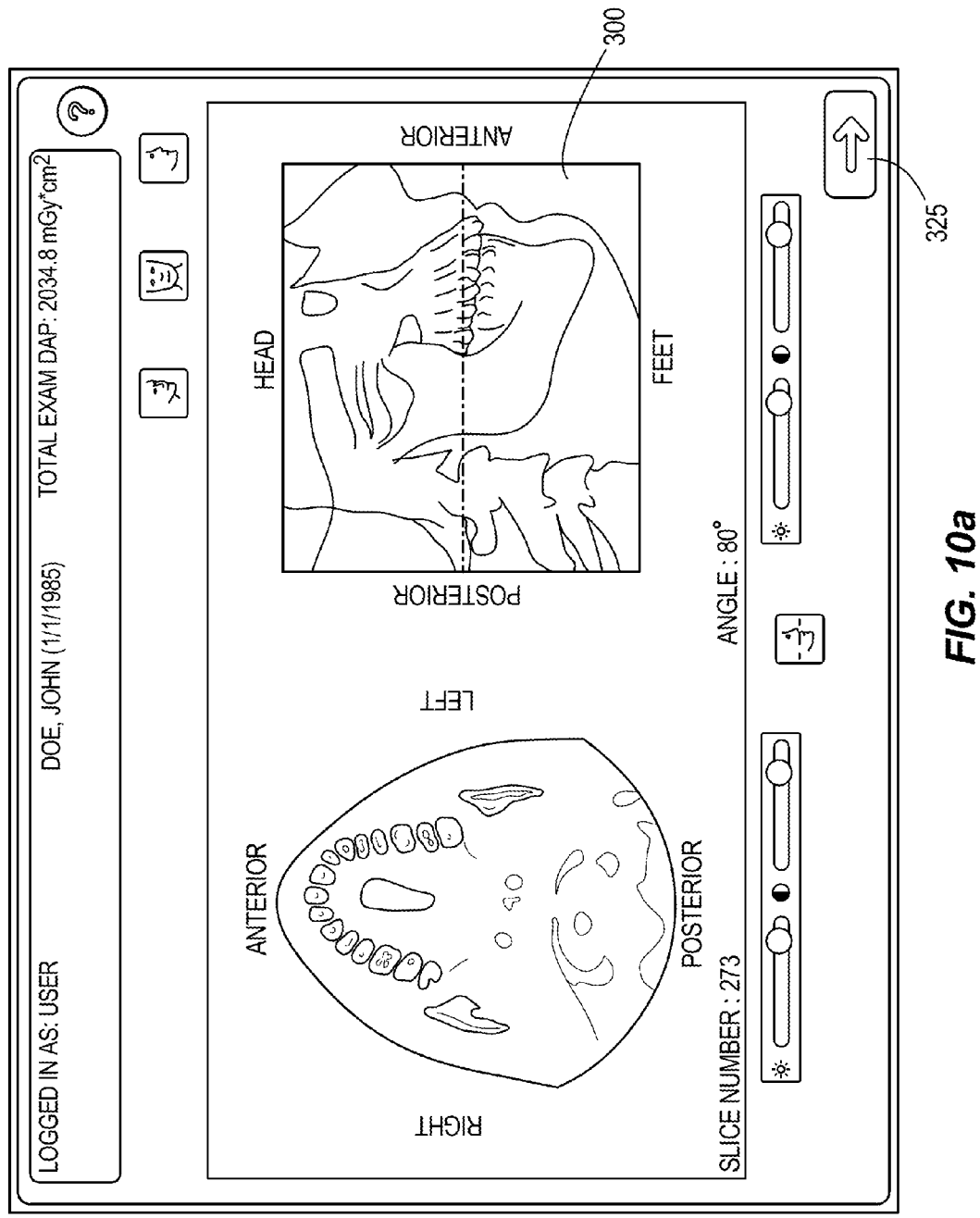
FIGS. 10a-10d illustrate a cinematic sequence.
Figure 10B:
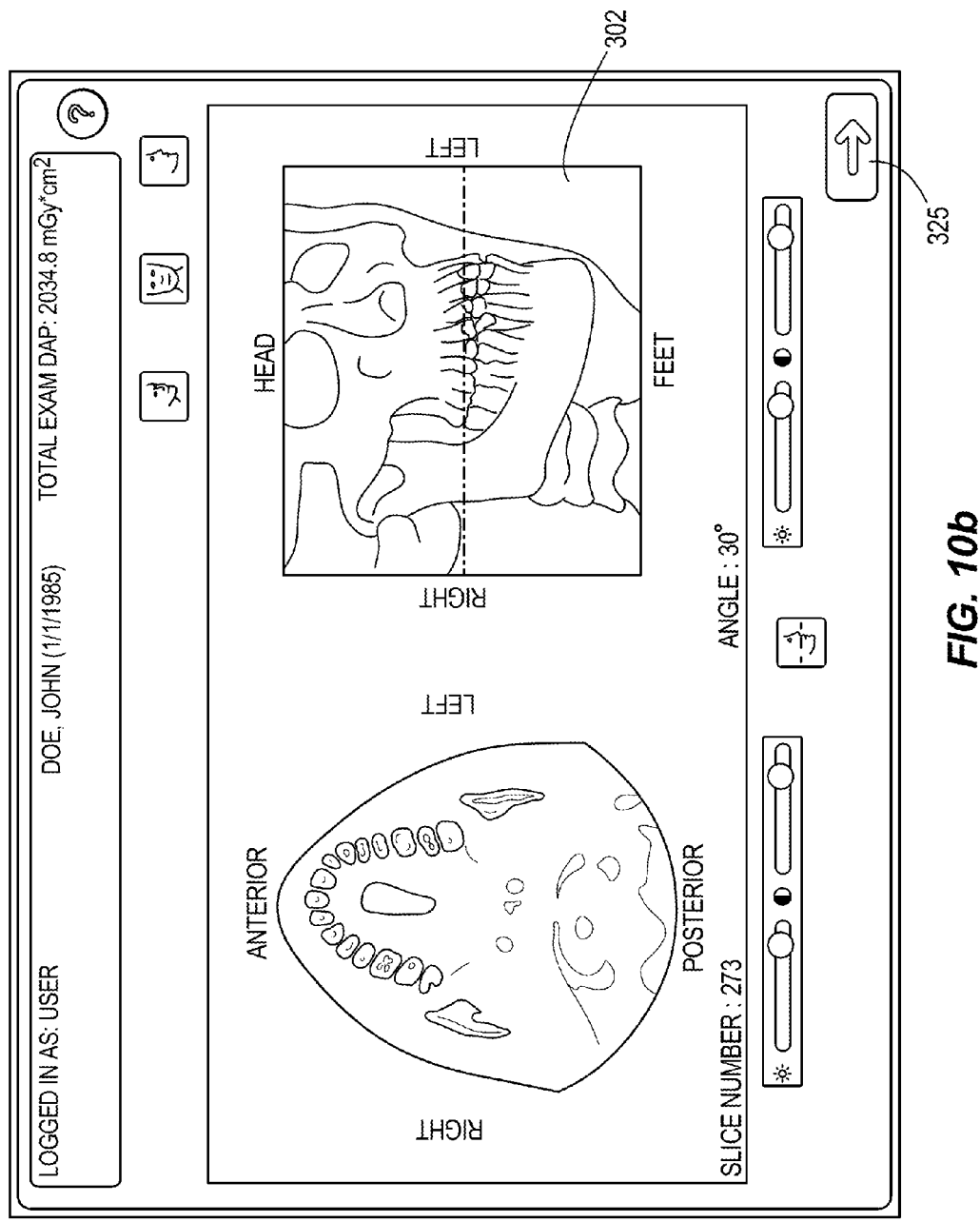
Figure 10C:
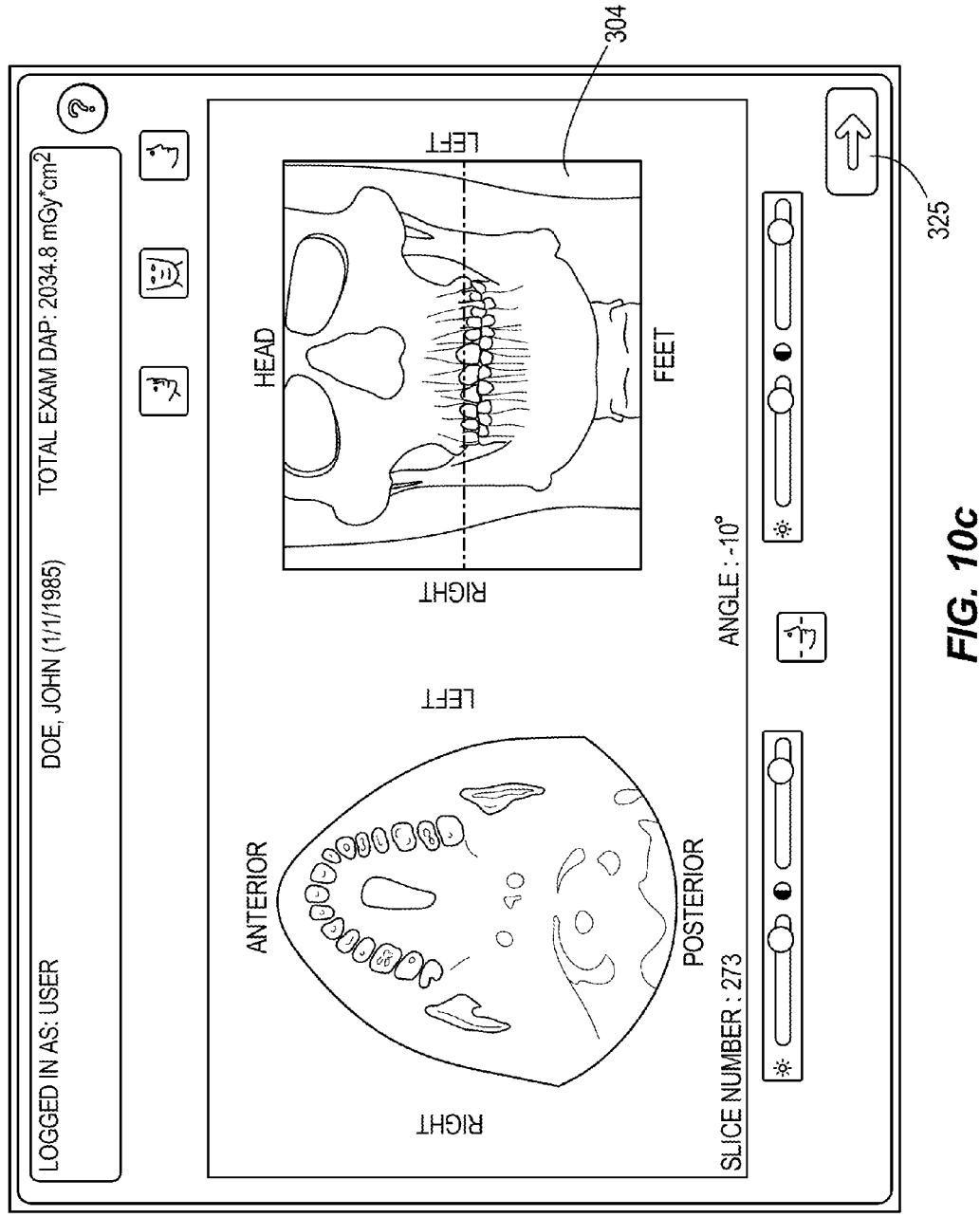
Figure 10D:
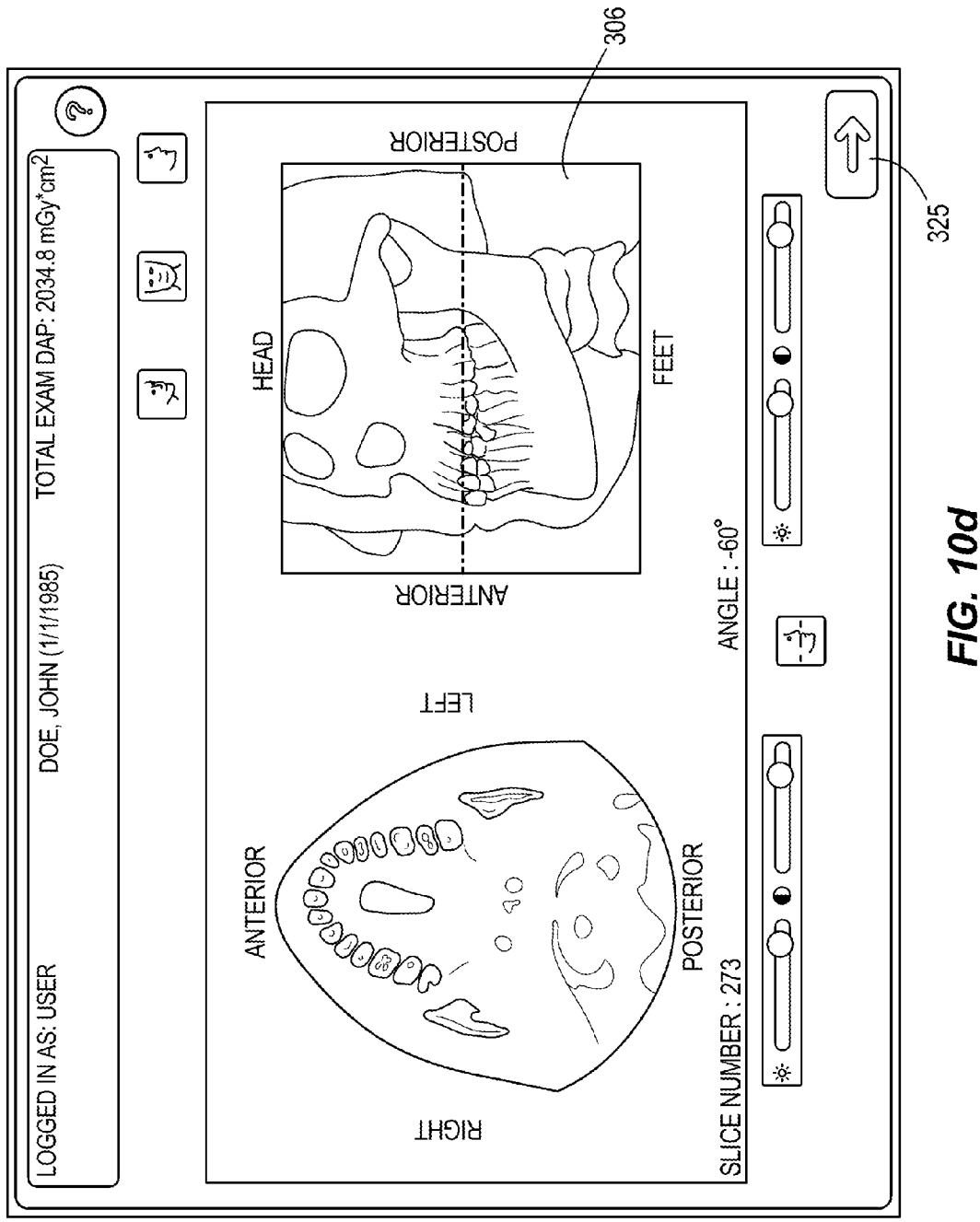

After generating the cinematic sequence, the application 210 generates a signal that displays the cinematic sequence on the touchscreen 110B (i.e., outputs the cinematic sequence to the touchscreen 110B) (at step 264). FIGS. 10a-d illustrate four sample frames of a cinematic sequence displayed by the application 210. As illustrated in FIGS. 10a-d, each of the cinematic frames has a parameter representing an angle of rotation of the patient's head (or angular vantage point of an observer of the patient's head) and the value of the parameter is different for each frame. For example, FIG. 10a illustrates a frame 300 of the cinematic sequence where the angle of rotation parameter has a value of approximately 0 degrees. FIG. 10b illustrates a frame 302 of the cinematic sequence where the angle of rotation parameter has a value of approximately 45 degrees. FIG. 10c illustrates a frame 304 of the cinematic sequence where the angle of rotation parameter has a value of approximately 90 degrees. FIG. 10d illustrates a frame 306 of the cinematic sequence where the angle of rotation parameter has a value of approximately 180 degrees. It should be understood that the cinematic frames illustrated in FIG. 10a-d represent sample frames from a cinematic sequence and that the cinematic sequence can include additional cinematic frames. Also, it should be understood that in some embodiments, the particular values for the parameter differentiating the cinematic frames are predefined for a particular parameter (e.g., 0, 45, 90, and 180 degrees). In other embodiments, a user sets the values before initiating a scan. The user-selected values can be set as a user's "favorites" as described above.

The application 210 automatically displays the cinematic frames 300, 302, 304, and 306 in a frame-by-frame manner. For example, the application 210 can be configured to display each cinematic frame for a predetermined amount of time (e.g., approximately 3 to 5 seconds) before displaying the next frame in the cinematic sequence. In some embodiments, the application 210 continuously displays the cinematic sequence until the application 210 receives a user command stopping the cinematic sequence. For example, returning to FIG. 3, while the cinematic sequence is displayed (at step 256), the user can determine whether he or she can properly assess the quality of the three-dimensional, volumetric data set based on the cinematic sequence (at step 310). If not, the user can stop the cinematic sequence and manually select particular aspects of the three-dimensional, volumetric data set (i.e., particular aspects of a volumetric image rendered from the three-dimensional, volumetric data set) (at step 320). For example, the user can select a next or stop button 325 (see FIGS. 10a-d) to stop displaying the cinematic sequence and view a subsequent screen where the user can request manual inspection and select the aspects of the three-dimensional, volumetric data set for inspection.

Figure 11:
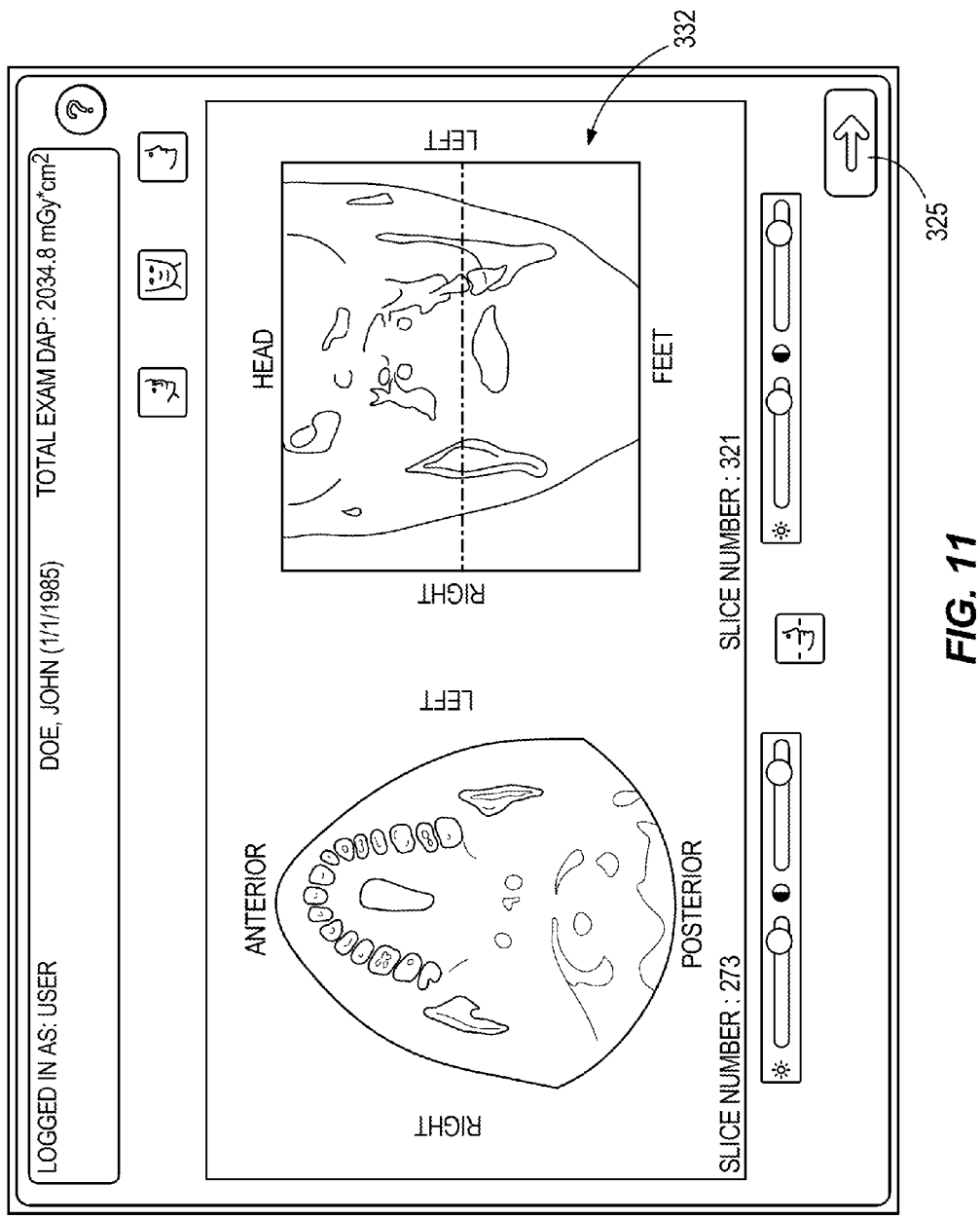
FIGS. 11 and 12 illustrate manual-inspection screens.
Figure 12:
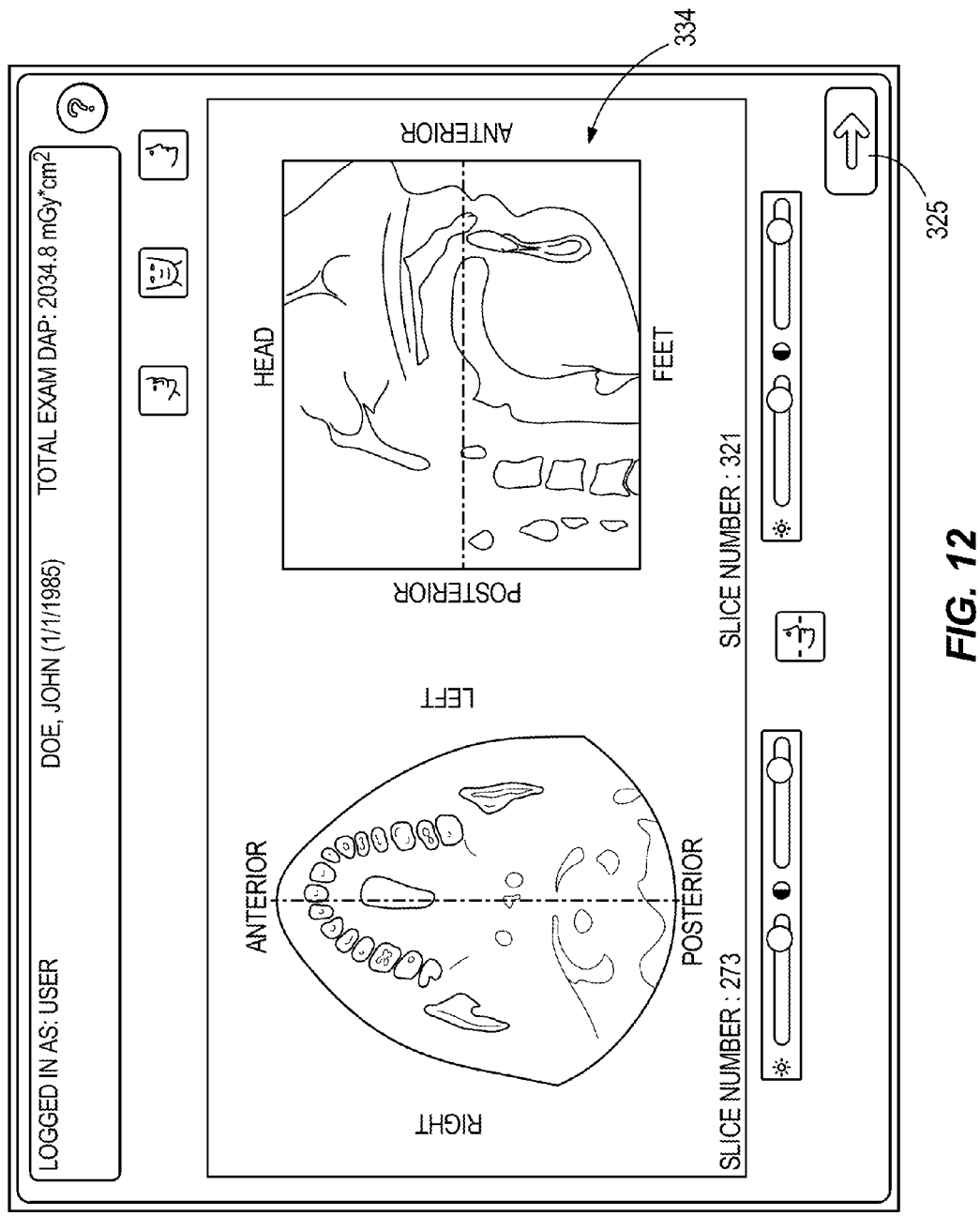

The application 210 displays the manually-selected aspects to the user (at step 330). For example, FIG. 11 illustrates a manually-selected coronal view 332 of a volumetric image, and FIG. 12 illustrates a manually-selected sagittal view of a volumetric image. The user can repeatedly manually-select different aspects or views until the user is able to properly assess the quality of the three-dimensional, volumetric data set acquired during the scan (at step 340). When the user has finished the manual inspection, the user can select a next or stop button 305 (see FIGS. 11 and 12), which provides the user with a subsequent screen where the user can either accept or reject the three-dimensional, volumetric data set acquired by the scan. As illustrated in FIGS. 11 and 12, during a manual inspection, the user can also adjust various display parameters of the selected views to assist in assessing image quality and positioning. In some embodiments, the user can similarly adjust the display parameters of the cinematic sequence.

When the user decides that the quality and positioning of the three-dimensional, volumetric data set (i.e., a volumetric image rendered from the three-dimensional data set) is proper (at step 350) (e.g., after solely viewing the cinematic sequence or after performing additional manual inspection), the user selects an accept button. Selecting the accept button instructs the application 210 to store the three-dimensional, volumetric data set to a storage location (e.g., external to the system 100) that can be accessed by other workstations and computers. Storing the data set ends the scan and allows the patient to exit the imaging apparatus 105. If the user decides that the quality or positioning of the acquired three-dimensional, volumetric data set is not proper, the user can re-initiate a scan as described above with respect to FIGS. 5-7.

It should be understood that although the application 210 is described as being used with a data set representing a scan of a patient's head (e.g., a jaw), the application 210 can be configured to generate cinematic frames to form a cinematic sequence for different purposes based on projection data generated based on a scan of any piece of anatomy or any object. In addition, other types of scanning procedures can be used to generate the projection data. In addition, in some embodiments, the functionality of the UI application 210 can be distributed among multiple applications or modules. For example, in some embodiments, the functionality of the application 210 is distributed between a first application or module that generates the cinematic frames of the cinematic sequence and a second application or module that generates the user interface that displays the cinematic sequence to a user and receives user commands.

Various features and advantages of the invention are set forth in the following claims.

What is claimed is:

1. A system for inspecting data generated during a scan of an object, the system comprising:
a processor configured to:
receive projection data generated by a CT scan of an object, generate three-dimensional, volumetric data based on the projection data, automatically compute a plurality of two-dimensional cinematic frames of a cinematic sequence based on the three-dimensional, volumetric data, wherein each of the plurality of two-dimensional cinematic frames represents a two-dimensional view of at least a subset of the three-dimensional, volumetric data, wherein each of the plurality of two-dimensional cinematic frames has a different value for at least one parameter, wherein the plurality of two-dimensional cinematic frames includes a plurality of slices of the three-dimensional, volumetric data, and wherein the at least one parameter includes a position within the object, and
automatically generate a signal to display different two-dimensional cinematic frames included in the plurality of two-dimensional cinematic sequentially one at a time.

2. The system of claim 1, wherein the processor is configured to automatically continuously display different two-dimensional cinematic frames included in the plurality of two-dimensional cinematic frames sequentially one at a time.

3. The system of claim 1, wherein the at least one parameter includes an angle of rotation of the object.

4. The system of claim 1, wherein the at least one parameter includes a magnification level.

5. The system of claim 1, wherein the at least one parameter includes a field-of-view.

6. The system of claim 1, wherein the at least one parameter includes a color.

7. The system of claim 1, wherein the at least one parameter includes a color scale.

8. The system of claim 1, wherein the at least one parameter includes a brightness level.

9. The system of claim 1, wherein the at least one parameter includes a contrast level.

10. The system of claim 1, wherein the at least one parameter includes a translational vantage point of the object.

11. The system of claim 1, wherein the processor is further configured to receive a stop command from a user and stop displaying the cinematic sequence.

12. The system of claim 1, wherein the processor is further configured to receive an accept command from a user and transfer the three-dimensional, volumetric data to a storage location in response to the accept command.

13. The system of claim 1, wherein the processor is further configured to receive a selection of the at least one parameter from a user prior to receiving the projection data.

14. The system of claim 13, wherein the selection includes at least one of a scan protocol selection and a scan type selection.

15. The system of claim 13, wherein the processor is configured to automatically generate the plurality of two-dimensional cinematic frames of the cinematic sequence based on the selection of the at least one parameter.

16. The system of claim 1, wherein the processor is further configured to provide manual inspection of the three-dimensional, volumetric data.

17. A method for inspecting data generated during a scan of an object, the method comprising:
receiving, at a processor, projection data generated by a CT scan of an object;
generating, by the processor, three-dimensional, volumetric data based on the projection data;
automatically, by the processor, computing a plurality of two-dimensional cinematic frames of a cinematic sequence based on the three-dimensional, volumetric data, wherein each of the plurality of two-dimensional cinematic frames represents a two-dimensional view of at least a subset of the three-dimensional, volumetric data, wherein each of the plurality of two-dimensional cinematic frames has a different value for at least one parameter, wherein the plurality of two-dimensional cinematic frames includes a plurality of slices of the three-dimensional, volumetric data, and wherein the at least one parameter includes a position within the object; and
automatically generate a signal to display different two-dimensional cinematic frames included in the plurality of two-dimensional cinematic frames sequentially one at a time.

18. The method of claim 17, wherein the at least one parameter includes an angle of rotation of the object.

19. The method of claim 17, wherein the at least one parameter includes a magnification level.

20. The method of claim 17, wherein the at least one parameter includes a field-of-view.

21. The method of claim 17, wherein the at least one parameter includes a color.

22. The method of claim 17, wherein the at least one parameter includes a color scale.

23. The method of claim 17, wherein the at least one parameter includes a brightness level.

24. The method of claim 17, wherein the at least one parameter includes a contrast level.

25. The method of claim 17, wherein the at least one parameter includes a translational vantage point of the object.

26. The method of claim 17, further comprising receiving a stop command from a user and stopping the cinematic sequence.

27. The method of claim 17, further comprising receiving an accept command from a user and storing the three-dimensional, volumetric data to a storage location in response to the accept command.

28. The method of claim 17, further comprising receiving a selection of the at least one parameter from a user prior to receiving the projection data.

29. The method of claim 28, wherein receiving the selection includes receiving at least one of a scan protocol selection and a scan type selection.

30. The method of claim 28, wherein automatically generating the plurality of two-dimensional cinematic frames includes automatically generating the plurality of two-dimensional cinematic frames based on the selection of the at least one parameter.

* * * * *